(12) United States Patent
Laduca (10) Patent No.: US 11,896,777 B2
(45) Date of Patent: Feb. 13, 2024

(54) DYNAMIC WALLED TUBING

(71) Applicant: QMAX, LLC, Santa Cruz, CA (US)

(72) Inventor: Robert C. Laduca, Santa Cruz, CA (US)

(73) Assignee: QMAX, LLC, Santa Cruz, CA (US)

( * ) Notice: Subject to any disclaimer, the term of this patent is extended or adjusted under 35 U.S.C. 154(b) by 0 days.

(21) Appl. No.: 17/409,215

(22) Filed: Aug. 23, 2021

(65) Prior Publication Data

US 2021/0379330 A1 Dec. 9, 2021

Related U.S. Application Data

(63) Continuation of application No. 15/825,986, filed on Nov. 29, 2017, now Pat. No. 11,123,517, which is a continuation of application No. PCT/US2016/035094, filed on May 31, 2016.

(60) Provisional application No. 62/168,610, filed on May 29, 2015.

(51) Int. Cl.
| | |
|---|---|
| *A61M 25/00* | (2006.01) |
| *A61L 29/12* | (2006.01) |
| *A61L 29/08* | (2006.01) |
| *A61L 29/14* | (2006.01) |
| *B29C 48/09* | (2019.01) |
| *B29L 31/00* | (2006.01) |
| *B29C 63/18* | (2006.01) |
| *B29C 63/42* | (2006.01) |
| *B29C 48/19* | (2019.01) |

(52) U.S. Cl.
CPC ....... *A61M 25/0023* (2013.01); *A61L 29/085* (2013.01); *A61L 29/12* (2013.01); *A61L 29/14* (2013.01); *A61M 25/0052* (2013.01); *A61M 2025/0024* (2013.01); *B29C 48/09* (2019.02); *B29C 48/19* (2019.02); *B29C 63/18* (2013.01); *B29C 63/42* (2013.01); *B29L 2031/7542* (2013.01)

(58) Field of Classification Search
CPC .......... A61M 25/0023; A61M 25/0052; A61M 2025/0024
See application file for complete search history.

(56) References Cited

U.S. PATENT DOCUMENTS

| | | | |
|---|---|---|---|
| 5,226,888 | A | 7/1993 | Arney |
| 5,538,510 | A | 7/1996 | Fontirroche et al. |
| 5,961,499 | A | 10/1999 | Bonutti et al. |
| 6,181,978 | B1 | 1/2001 | Hinds |
| 6,186,978 | B1 | 2/2001 | Samson et al. |
| 6,352,238 | B1 | 3/2002 | Roman |
| 6,358,238 | B1 * | 3/2002 | Sherry ................ A61M 25/005 604/524 |
| 11,123,517 | B2 | 9/2021 | Laduca |
| 2007/0088319 | A1 | 4/2007 | Martone |
| 2009/0105641 | A1 | 4/2009 | Nissl |
| 2009/0209969 | A1 * | 8/2009 | Wolfe ................ A61B 17/3439 606/108 |

(Continued)

FOREIGN PATENT DOCUMENTS

| | | |
|---|---|---|
| CN | 102573709 | 7/2012 |
| CN | 203736693 | 7/2014 |

(Continued)

*Primary Examiner* — Dung T Ulsh
(74) *Attorney, Agent, or Firm* — Levine Bagade Han LLP (57) ABSTRACT

Methods and devices described for improved dynamic walled tubing and catheters.

23 Claims, 9 Drawing Sheets

(56) References Cited

U.S. PATENT DOCUMENTS

| | | |
|---|---|---|
| 2009/0240202 A1 | 9/2009 | Drasler et al. |
| 2010/0094392 A1* | 4/2010 | Nguyen ............ A61M 25/0023 |
| | | 623/1.11 |
| 2011/0264133 A1 | 10/2011 | Hanlon et al. |
| 2012/0283633 A1 | 11/2012 | von Hoffmann |
| 2014/0121629 A1 | 5/2014 | Macaulay et al. |
| 2014/0142509 A1 | 5/2014 | Bonutti et al. |
| 2014/0236122 A1* | 8/2014 | Anderson ......... A61M 25/0012 |
| | | 604/523 |
| 2018/0169378 A1 | 6/2018 | Laduca |

FOREIGN PATENT DOCUMENTS

| | | |
|---|---|---|
| DE | 102005034529 | 1/2007 |
| JP | 2003-508132 | 3/2003 |
| JP | 2004-515255 | 5/2004 |
| JP | 2008-538709 | 11/2008 |
| JP | 2010-227137 | 10/2010 |
| JP | 2012-513294 | 6/2012 |
| JP | 2013-542006 | 11/2013 |
| JP | 2014-511202 | 5/2014 |
| WO | WO 2001/015763 | 3/2001 |
| WO | WO 2016/196511 | 12/2016 |

\* cited by examiner

DYNAMIC WALLED TUBING

CROSS-REFERENCE TO RELATED APPLICATIONS

This application is a continuation of U.S. patent application Ser. No. 15/825,986 filed Nov. 29, 2017, which is a continuation of PCT application PCT/US2016/035094 filed May 31, 2016, which claims the benefit of priority to U.S. Provisional Application No. 62/168,610 filed May 29, 2015, the content of each of which is incorporated herein by reference in its entirety for all purposes.

BACKGROUND OF THE INVENTION

There remains a need for improved medical devices having tubing useful for such applications as access devices, catheters, introducers, or other such devices intended to provide access to regions within the body. For example, such devices can include dynamic wall structures that readily expand to allow passage of other medical devices, components, and/or implants where the dynamic wall returns to its normal diameter after passage of the secondary medical device, component and/or implant. Such dynamic wall structures can include active dynamic wall tubing where the expansion of the tubing requires activation. Alternatively, such dynamic wall structures can be passive where the tubing expands and contracts to accommodate passage of devices through the structure.

SUMMARY

The present disclosure includes expandable tubing configuration. In one example, the tubing comprises an outer tube body comprising an expandable material; a structural element positioned helically within a wall of the outer tube body, where the structural element is expandable in an axial length, such that expansion of the structural element in the axial direction expands a diameter of the outer tube body.

In an additional variation, the structural element is configured to be pressurized. A variation of the structural element comprises a coil or braid.

The structural element can comprise a wire or a polymeric material or a combination of both. In one example, the structural element comprises a first polymer and a second polymer co-extrusion such that a second of the structural element can comprise differing structural properties than the remainder of the section. Such properties can include durometer, elasticity, degree of stretchability, etc.

In an additional variation, the structural element comprises a curved configuration in an unexpanded shape and straightens when expanded.

In an additional variation, the structural element comprises a series of spring material having a zig-zag or undulating configuration when helically located within the wall of the outer tube body. Such a configuration can include a nested configuration.

In an additional variation, the outer tube body comprises a tubing material and a secondary material co-extruded with the tubing material. In such a configuration the secondary material stretches to a greater degree than the tubing material when the outer tube body expands. The outer tube can have any number of sections of the secondary material.

In any of the variations, the expandable tubing can have an expandable tip configuration.

DETAILED DESCRIPTION OF THE INVENTION

The following illustrations demonstrate various embodiments and examples of the devices and methods according to the present disclosure. Combinations of aspects of the various devices and methods or combinations of the devices and methods themselves are considered to be within the scope of this disclosure.

Figure 1A:
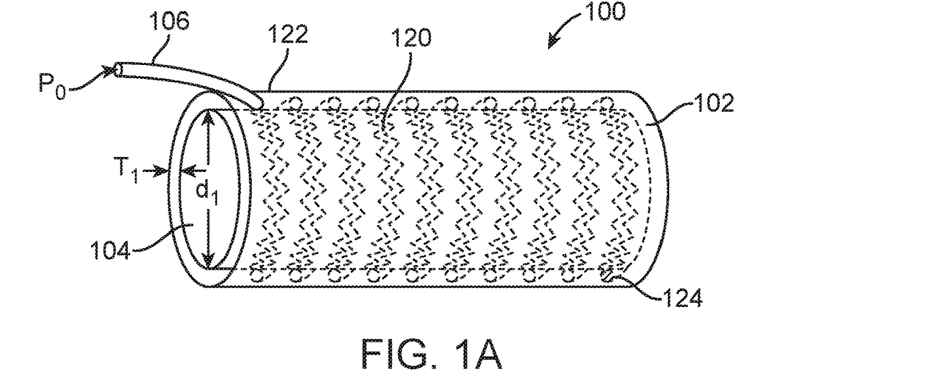
FIG. 1A illustrates one example of an expandable tube configuration.

FIG. 1A illustrates one example of an expandable tube configuration 100 having an outer tube body 102 having a wall of thickness T1 and a lumen 104 with diameter d1. The tube body 102 is fabricated from an expandable polymer material with a structural element 120 located therein. The structural element 120 functions to assist the outer tube body 102 in expanding when an oversized device (not shown) is passed through the lumen. The structural element can be embedded with in the wall of the tube body 102 such as through an extrusion or molding process. Alternatively, the structural element 20 can be positioned within a channel extending through the wall of the tube body 102.

Figure 1B:
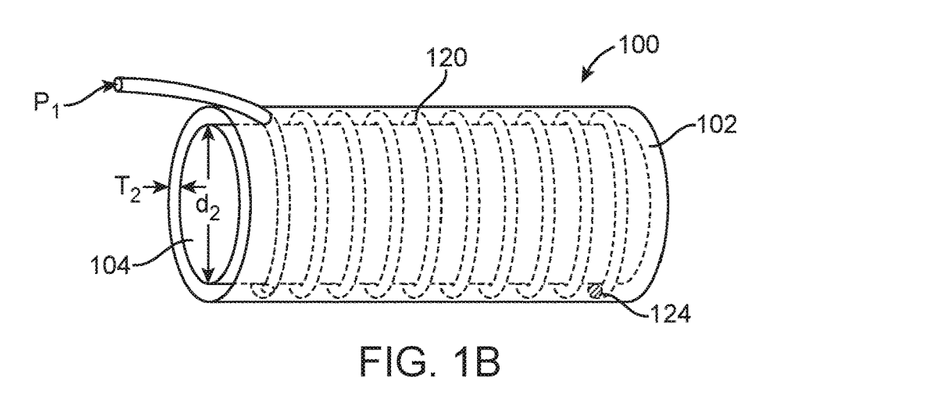
FIG. 1B shows the expansion of the structural element allows the expandable tube when located within the tube body.
Figure 1C:
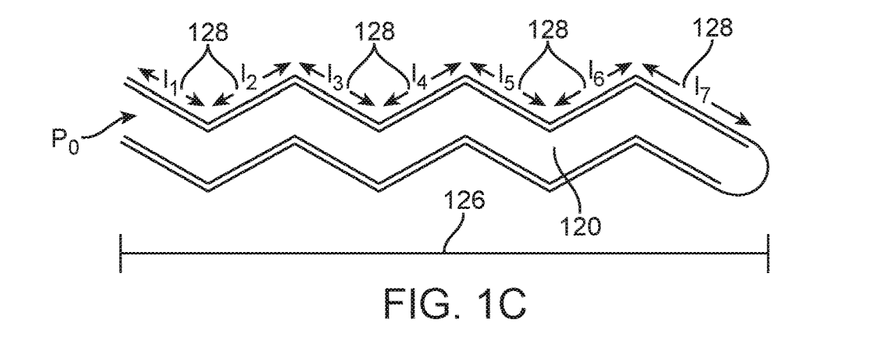
FIG. 1C illustrates a structural element prior to expansion.
Figure 1D:
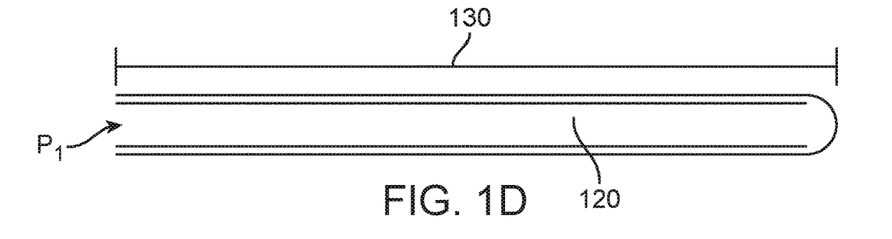
FIG. 1D illustrates a structural element after expansion.

In the variation illustrated in FIG. 1A, the structural element 120 comprises a wavy, zig-zag, or oscillating shape, as shown in FIG. 1C. Where the function of the shape is such that the total length 126 of the element 120 is reduced and can be expanded, as shown in FIG. 1D to an increased length 130 upon actuation of the structural element 120. In certain variations, the length of each segmented section 128 comprises the elongated length 130. In additional variations, the structural element 120 can be elastically expandable along length 126 to achieve increased length 130. In the illustrated variation, the structural element 120 can comprise an elastic structure that can be pressurized from a baseline pressure P0 to an increased pressure P1 where the increased pressure straightens the structural element from length 126 to 130. Clearly, alternate modes of expanding the length are within the scope of variations of this disclosure. For example, the structural element can comprise a shape memory alloy that is heat or energy activated to expand from its natural length 126 to its expanded length 130. Furthermore, the structural element 120 can include any number of shaped configurations apart from a zig-zag, wavy, or oscillating shape as long as the length can increase as desired.

FIG. 1A illustrates a state of the expandable tube 100 when the structural element 120 is in a natural or unextended state. The illustrated variation shows an inflation tube 106 coupled to the structural element 122. Any number of valves and/or plugs 124 can be used on either end of the structural element 122.

Alternate variations of the device include an inflation tube being a part of the structural element 122. In the initial condition, the pressure P0 allows the structural element 122 to remain in a relaxed condition where the diameter of the lumen 104 remains at d1. When desired, pressure is increased within the inflation tube 106 and/or structural element 120 as represented by P1. This increase in pressure permits the structural element 120 to extend from its initial state (as shown in FIG. 1C) to its elongated or extended state (as shown in FIG. 1D). The corresponding change of the length of the structural element 120 from 126 to 130 acts upon the tube body 120 to increase a diameter of the lumen 104 to D2. In certain variations the thickness T1 of the wall of the tube body 102 in the natural state remains the same or approximately the same as a thickness T2 of the wall in the expanded state. Alternate variations include devices where the thickness of the device varies between expanded and unexpanded states.

FIG. 1B shows how expansion of the structural element 122, drives expansion of the expandable tube 102. As noted above, this variation can be considered to be an actively expandable tube 100 where the stress inducing compressed zig zag structural element 120 can be actuated to expand a diameter of the tube body 102 to allow passage of an oversized device into the lumen. When pressurized, the structural element 120 straightens and adds length to the circumference via an expanding diameter while allowing the wall thickness T2 to remain the same or nearly the same as the unexpanded wall thickness T1 of the unexpanded tube 100.

Additional variations of the device 100 can include multiple structural elements 120 positioned within the wall of the expandable tube 102. In addition, one or more structural elements 120 can be positioned within or about the tube 102 if desired.

Figure 2A:
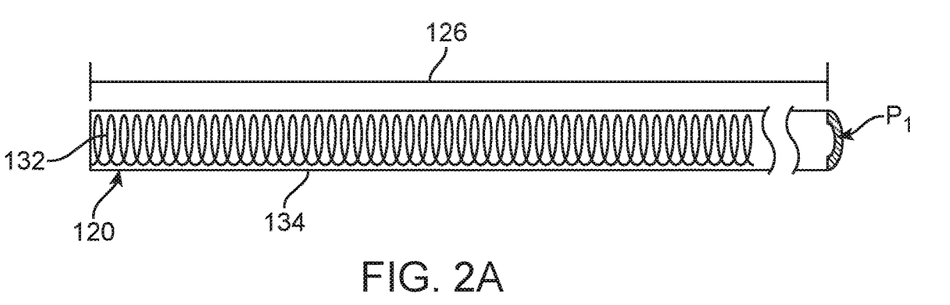
FIG. 2A illustrates another variation of a structural element prior to expansion but in a linear configuration.
Figure 2B:
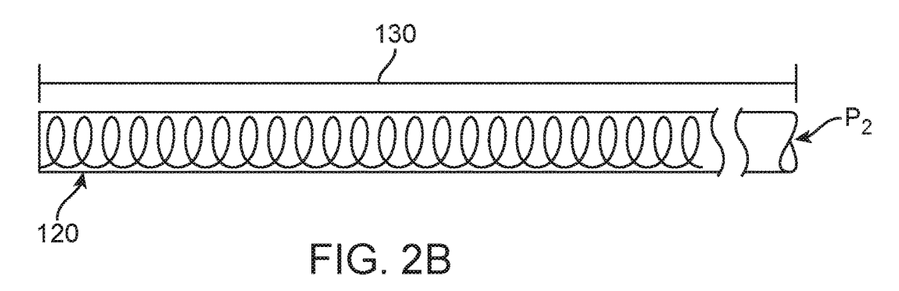
FIG. 2B illustrates the variation of the structural element in FIG. 2A after expansion.
Figure 2C:
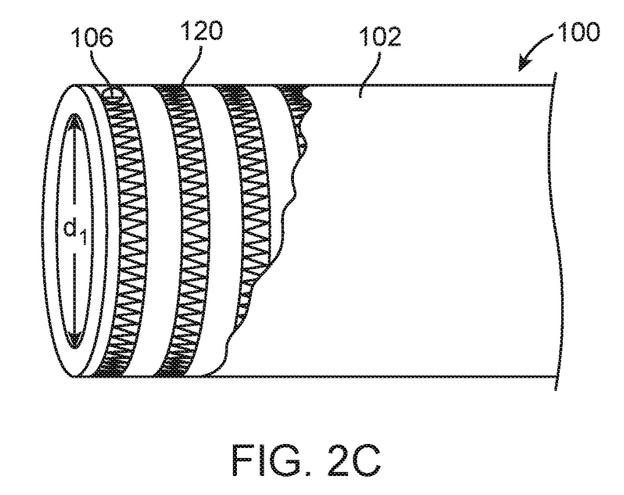
FIG. 2C shows a partial cut-away portion of a dynamic walled tubing with the structural element in a non-extended or non-expanded configuration.
Figure 2D:
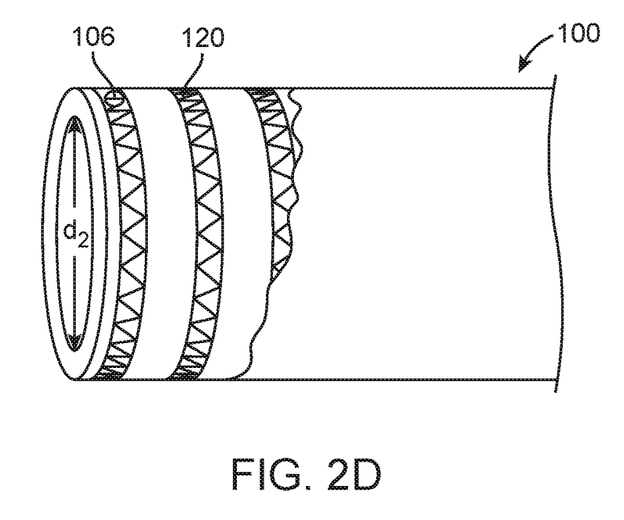
FIG. 2D shows a partial cut-away portion of the dynamic walled tubing with the structural element in an extended or expanded configuration.

FIG. 2A-2C illustrate another variation of a structural element 120 for use in a device 100 having dynamic walled tubing. In this variation, as shown in FIG. 2A, the structural element 120 is linear and comprises a coil or braid 132 located within an expandable liner 134. In the natural state, as shown by FIG. 2A, the liner 134 is at a first pressure P1 which corresponds to a first length 126. Upon pressurization, to P2, the liner and coil expand to length 130. Once pressure returns to P1, the coil 132 and the liner 134 return to the state as shown by FIG. 2A.

FIG. 2C shows a cut-away portion of a dynamic walled tubing 100. As illustrated, the structural element of FIG. 2A is helically positioned within a wall of a tube body 102. As the structural element is pressurized via a port 106, the structural element 120 expands in length (as shown in FIG. 2B) such that the dynamic walled tubing 100 expands to the configuration shown in FIG. 2C. Again, the diameter of a lumen 104 in the tubing 100 can increase from d1 to d2 or any range therebetween. When pressure within the structural element 120 is reduced, the dynamic walled tubing 100 can return to the state depicted in FIG. 2C.

Figure 3A:
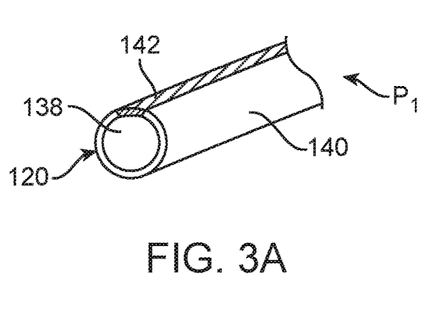
FIGS. 3A-3G illustrate another variation of a structural element 120 for use with a dynamic walled tubing.
Figure 3B:
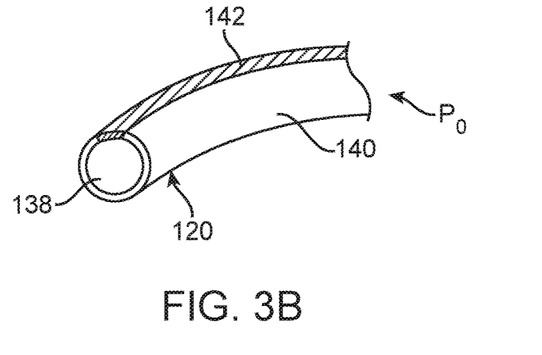
Figure 3C:
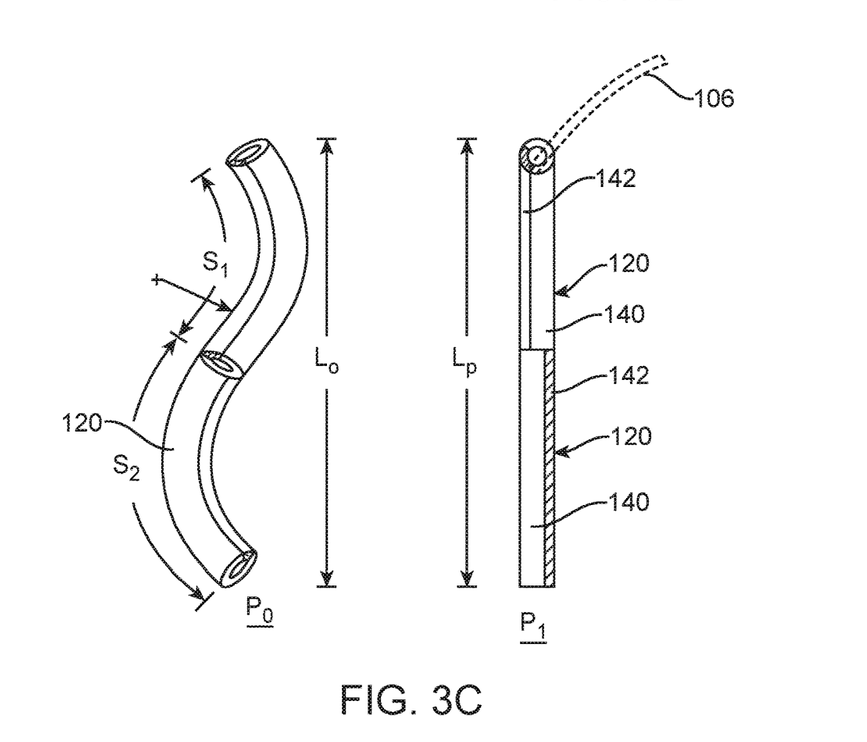

FIGS. 3A-3G illustrate another variation of a structural element 120 for use with a dynamic walled tubing 100. FIGS. 3A and 3B show a structural element comprising a first polymer 140 and a second polymer 142 where the first and second polymers 140 142 have differing structural properties such as durometer, elasticity, etc. In the illustrated example, and as shown with alternate configurations of the structural elements described herein, the structural element 120 can be configured to be pressurized, e.g., by sealing one or both ends of the lumen 138 and using an inflation member 106 (shown in FIG. 3C). With such a configuration, at a standard pressure P0, the structural element is in the configuration of FIG. 3B, e.g. a curved configuration, due to the differing structural properties of the first and second polymers 140 142. Upon pressurization of the element 120 to P1 the structural element straightens as shown in FIG. 3A. FIG. 3C shows the configuration of P0 on the left and P1 on the right where the structural element 120 goes from a shortened length L0 to an extended length L1.

As shown in FIG. 3C the second polymer 142 can be intermittent along the length of the structural element 120. In the illustrated variation, the second polymer 142 is located on opposite circumferential sides of the structural element 120. However, alternate variations are within the scope of this disclosure such as opposing helical winds, multiple strips along the structural element, etc. The variation shown in FIG. 3C illustrates the second polymer 142 forming two arcuate shapes that form a completed wave structure at P0.

In FIGS. 3A to 3C, the second polymer 142 comprises a lower modulus elastic strip where each opposing strip is aligned to be on a concave part of the waveform (inner part of the curve). When the structural element 120 is pressurized the stripe elongates and straightens the waveform by the anisitropic elastic modulus property of the intermittently stripped dual material tubing. One end of the helically wrapped intermittently striped waveform tubing is sealed. The other end has an extension line 106 with a port for attaching to a pressure source. For medical applications the port could be a luer fitting and the pressure source a syringe or other inflation device.

Figure 3D:
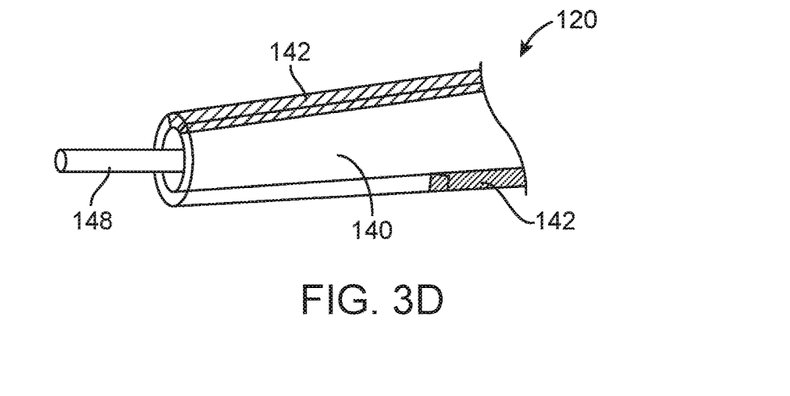

FIG. 3D illustrates the structural element 120 to have a reinforcing element 148 coupled to the structural element 120 (in this variation the reinforcing element 148 is inside the structural element 120. Such a configuration increases a kink resistance, hoop strength, buckling strength, crush resistance, torque transmission, burst strength, and pushability of the structural element 120. The reinforcing element 148 can be metal or polymer, single solid form or multi stranded cable or fiber bundle, stainless steel or nitinol, shape set or superelastic.

Figure 3E:
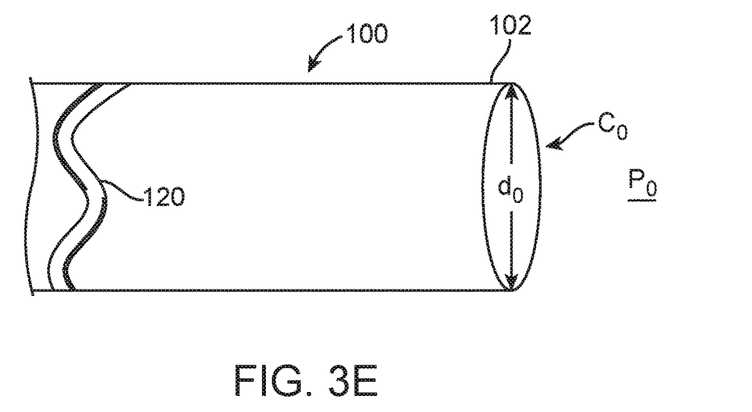

FIG. 3E illustrates the structural element 120 coupled to a tube body 102 where the structural element 120 is wrapped in a wave pattern and wound continuously in a helical pattern about a circumference C0 of the tube body 102 such that the internal diameter of the expandable tube 100 is d0.

In an additional variation, the striped structural element described above can be crosslinked so that it doesn't melt during a thermal fusing process used to create the structure. The amount of crosslinking can be controlled in a subsequent crosslinking initiation process such as exposure to UV energy, electron beam, gamma, x-ray, microwave, or other radiation source. The tubing resins can be compounded with a crosslinking inducing agent prior to the coextrusion process used to produce the dual durometer tubing. The amount or type of crosslinking initiator can be varied in the compounding step to achieve varying degrees of crosslinking upon exposure to crosslinking energy.

The crosslinking of the structure is not a necessary requirement for thermally fusing the wrapped tubing because the intermittent striped tubing material can be composed of a higher melting point than the materials used in the liner and jacket of the resultant structure. The jacket material is not required to chemically bond to the intermittent striped structural element so for example the jacket and/or liner may be composed of a polyurethane, silicone, or other elastomer and the striped tubing composed of PEBA resin, polyethylene, PET, or other thermoplastic.

Figure 3F:
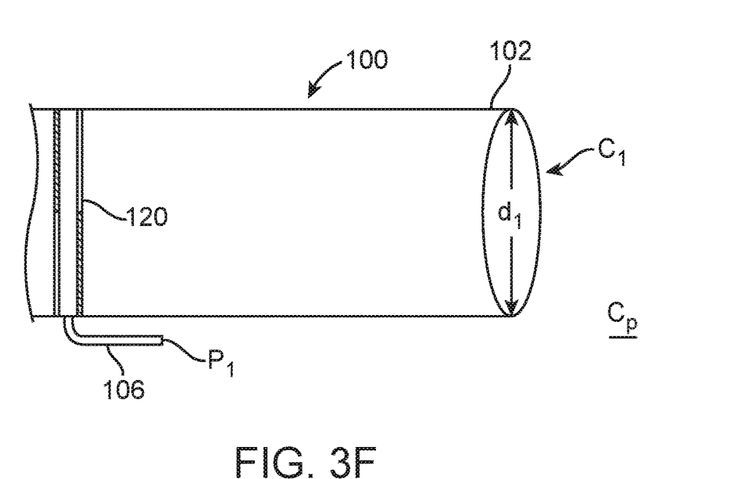

FIG. 3F illustrates increasing pressure to P1 within structural element 120 to increase the diameter of the expandable tube 100 to d1. As noted herein the internal diameter d1 of the resultant structure 100 expands upon the application of pressure to the wrapped stripped tubing resulting in a larger pressurized circumference C1. While there is only one structural element 120 shown in FIG. 3F any number of structural elements 120 can be used along the axis of the tube 102. In certain variations multiple structural elements can be wrapped about the tube 102. In certain variations, the outer diameter of the structural element being wrapped and the number of structural elements being wrapped determines the helix angle. Moreover, a continuous structural element 120 can be wrapped along an axis of the tube 102.

Figure 3G:
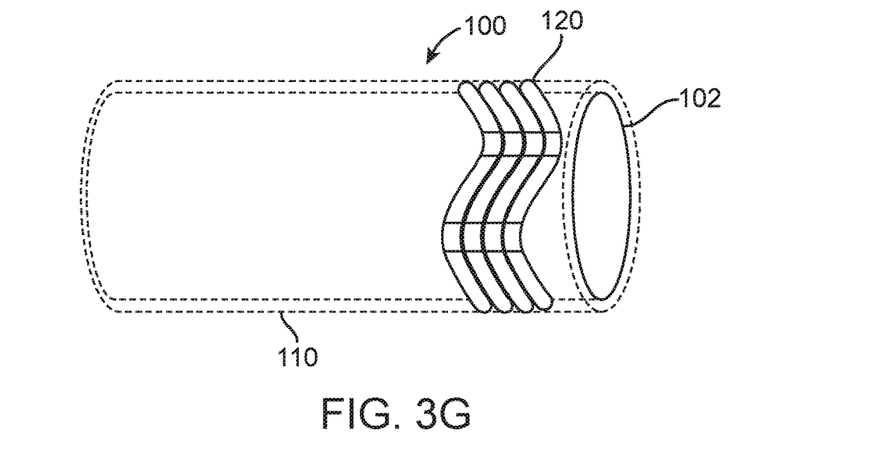

FIG. 3G shows a variation of an expandable tubing 100 as described herein being constructed. FIG. 3G shows a structural element 120 (or plurality of structural elements) being wrapped about a tube 102. The wrapped tube can then be jacketed with a polymer layer or liner 110 to hold the structure together. Alternatively or in combination, the structural element 120 and inner tubing 102 can be bonded to each other along the surfaces of contact. The tubing 100 may have a square or rectangular cross section rather than the round cross section as illustrated. There may also be a liner on the internal surface of the structure that will stretch to increase in diameter when the structure is pressurized. This liner may be made of a thin lubricious material such as PTFE or other more elastic polymers with or without coating applied to the inner surface. The fusing of the wrapped tubing with a liner and jacket can be a thermal process such as lamination, lasering, ultrasonic, electromagnetic induction or radiofrequency bonding. The fusing may be done with or without the use of external processing aids such as removable heat shrink tubing or internal processing aids such as removable mandrels.

In another variation, fusing of the wrapped structural element 120 about the tubing 102 and liner 110 can be accomplished by a liquid dispersion process such as dipping in a solution of solvated polymer and allowing the solvent to evaporate. The resultant tubing structure 100 could be configured with a tapered tip for insertion into blood vessels or mating with dilators or obturators, or it may have a balloon mounted to the tip on the outer surface to provide retention force to resist tensile loads or to provide a seal for either vacuum, pressure, or fluid or gas transfer. In addition to a balloon on the outer surface, or independently, a balloon may mounted to the internal surface over a portion of the length of one end of the structure to provide a seal either for vacuum, pressure, or fluid or gas transfer.

Figure 4A:
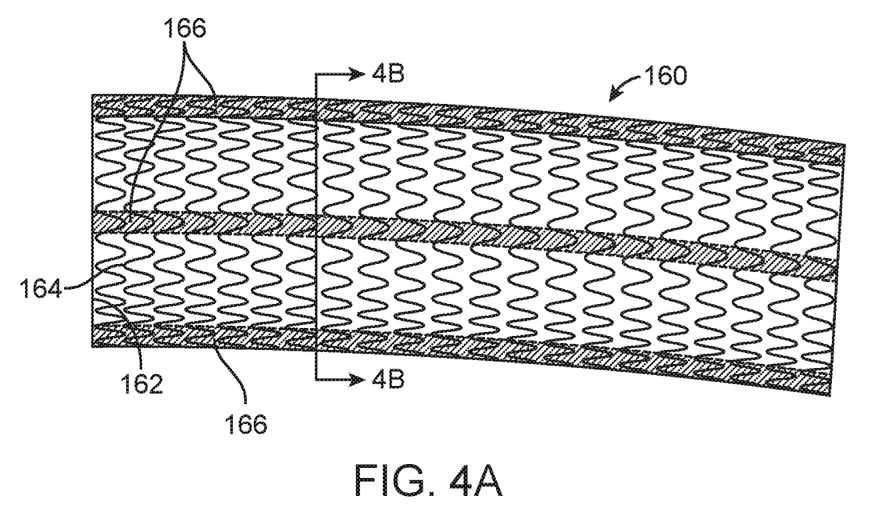
FIG. 4A illustrates another variation of a passive dynamic walled tube.

FIG. 4A illustrates another variation of a passive dynamic walled tube 160. As shown, the dynamic walled tube 160 includes a series of spring material 164, such as a wire. In this variation, the spring material 164 comprises a nested wire wound in a zig-zag manner within a body of the tubing 160. The properties of the spring material 164 can be consistent or vary through the tubing. Furthermore, the amplitude of the spring material 164, the pitch of the wire, the number of turns, as well as other material parameters can be adjusted as needed through the length of the tubing 160. The dynamic tubing also includes one or more regions of a secondary material 166 extending through the tubing that comprises structural properties different than a remainder of the tubing material 162. For example, the tubing material 162 can comprise a HDPE/LDPE or a blend thereof. While the strip material 166 can comprise a low flexural modulus material, such as a PolyBlend 45A material.

Figure 4B:
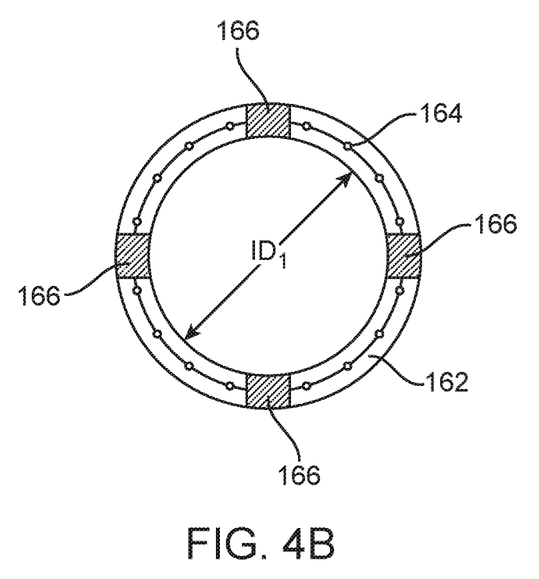
FIG. 4B illustrates a cross sectional view of the tube of FIG. 4A taken along line 4B-4B.

FIG. 4B illustrates a cross sectional view taken along the lines 4B-4B of FIG. 4A. As shown, the tubing material 162 and secondary material 166 can be co-extruded around or on the reinforcing spring material 164. The spring material 164 is constrained from an expanded state when extruded or formed into the tubing material 162 and secondary material 166. Because the tubing material 162 and secondary material 166 constrains the spring material 164, the spring material 164 will reduce the force required to expand the dynamic walled tube 160 when a device is placed therethrough. In other words, as the dynamic walled tubing expands due to passage of a device therein, the spring material 164 attempts to revert to its expanded state thereby lessening the force required to expand the dynamic walled tubing and reducing the force required to advance the device through the dynamic walled tubing. However, upon removal of the device within the dynamic wall tubing 160 allows the tubing material 162 and secondary material 166 to again constrain the spring material 164 and revert to the natural state shown in FIG. 4A.

Figure 4C:
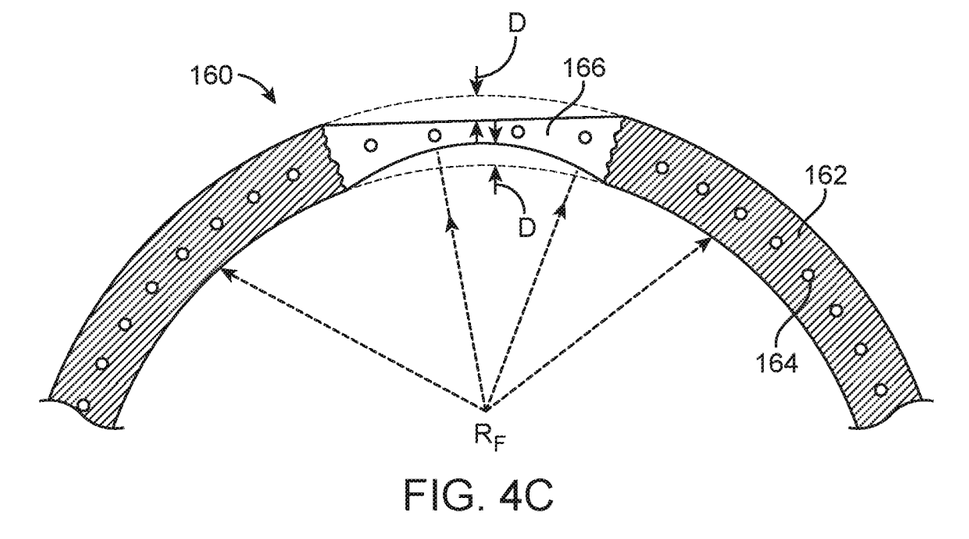
FIG. 4C illustrates the dynamic walled tubing of FIGS. 4A and 4B to illustrate a radial force that represents passage of a device through the lumen of the dynamic walled tubing.

FIG. 4C illustrates the dynamic walled tubing 160 of FIGS. 4A and 4B to illustrate a radial force RF that represents passage of a device through the lumen of the dynamic walled tubing 160. The radial force RF causes stretching of the secondary material 166, which in certain variations, is more elastic than the tubing material 162. As illustrated, the stretching of the secondary material 166 causes deflection of the wall thickness of the secondary material 166 by an amount D while the wall tubing 162 thickness remains substantially unchanged. As noted above, the stored energy of the nested coil 164 functions to reduce the amount of radial force RF required to expand the dynamic walled tubing 160 at the region of the secondary material 166. The stretching and deflection of the secondary material 166 also serves to reduce a contact surface area between the dynamic walled tubing and the device advanced therethrough and further reduces the amount of force required to advance the device through the dynamic walled tubing 260.

Figure 4D:
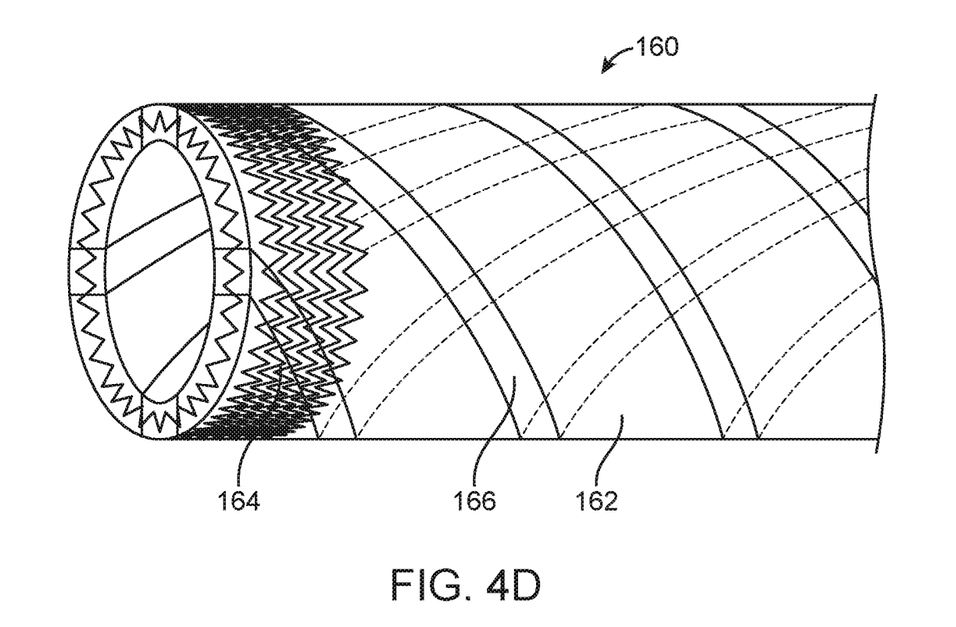
FIG. 4D illustrates another variation of a dynamic walled tubing with a secondary material that extends in a helical configuration about the tubing.

FIG. 4D illustrates another variation of a dynamic walled tubing 160. In this variation, the secondary material 166 extends in a helical configuration about the tubing 160.

Figure 5A:
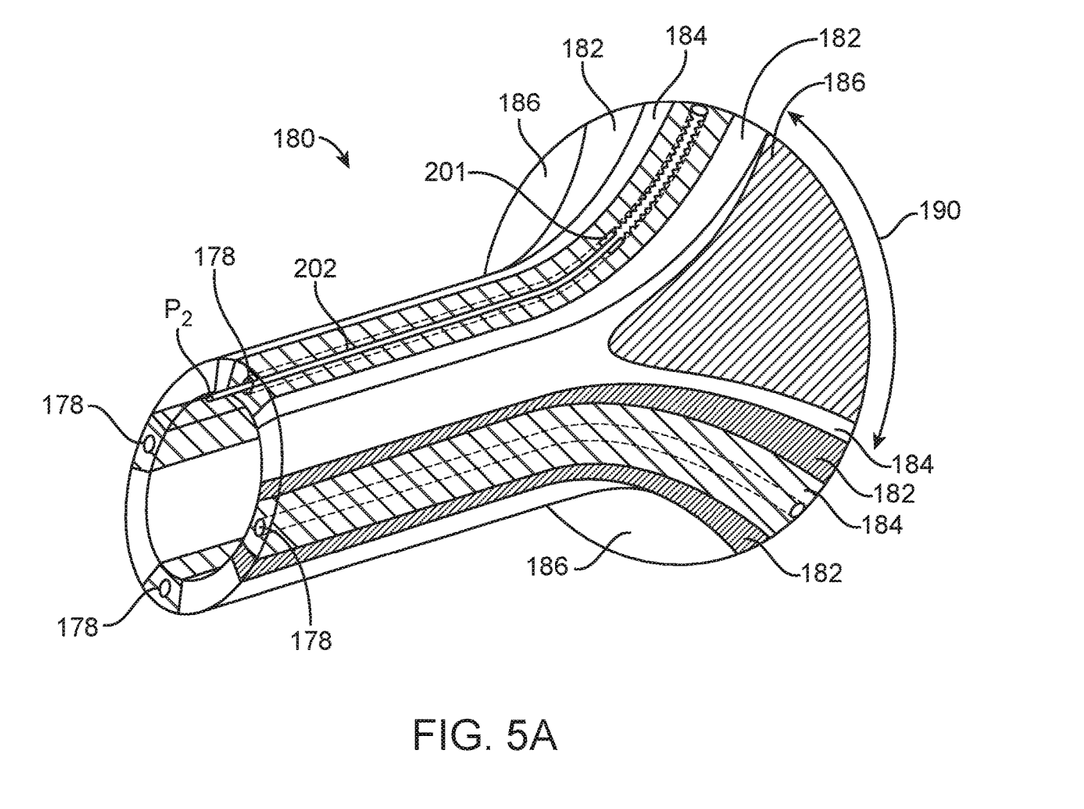
FIG. 5A illustrates another variation of a dynamic walled tube configured to have an expandable tip.

FIG. 5A illustrates another variation of a dynamic walled tube configured to have an expandable tip. As shown, the tip of the tube 180 comprises a first material 184, typically a lower durometer material (e.g., 40A), containing a lumen 178 extending therethrough and terminating at the tip. A second material 182 higher durometer material (e.g., greater than 80A) is located adjacent to the first material 184. Next, a highly elastic material 186 is located adjacent to the second material 182. To expand the tip, a mechanism 202 causes elongation of the first material 184. Because the second 182 material is difficult to elongate, the highly elastic material 186 stretches allowing materials 184 and 182 to expand outwards causing the tip to expand as shown by arrow 190.

Figure 5B:
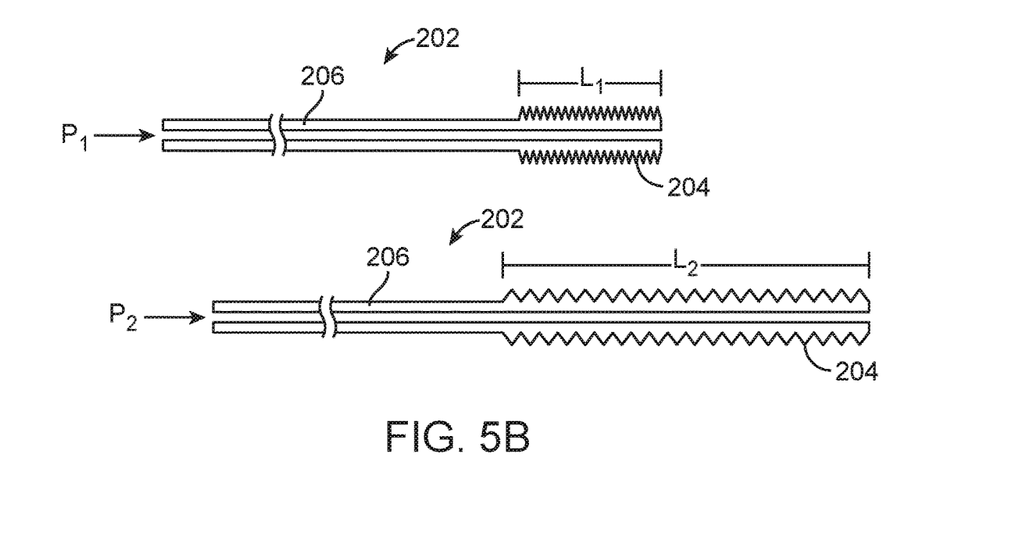
FIG. 5B shows an extension mechanism to expand the tip of the device of FIG. 5A.
Figure 5C:
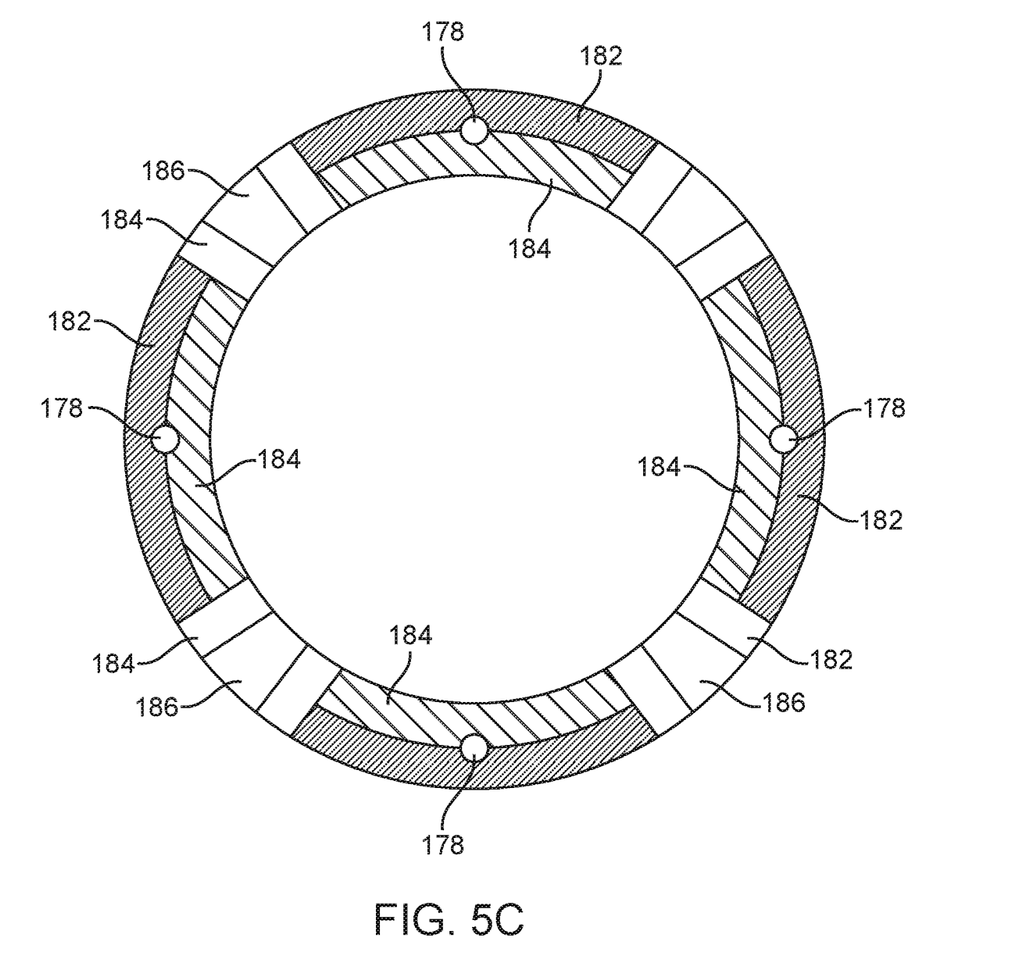
FIG. 5C shows a cross sectional view of the tip of the expandable tip catheter when in a non-expanded configuration.

FIG. 5B illustrates one example of mechanism for expanding the expandable tip catheter shown in FIG. 5A. In this example, the mechanism 202 comprises a thin walled longitudinally expandable pressure tubing. In additional variations, the tubing is not limited to longitudinal expansion but effectively expands to cause a distal force on the tip of the catheter 180 when located in the lumen 178, which results in expansion of the tip of the catheter 180.rAs shown, tubing comprises a non-expandable section 205 adjacent to an expandable section 204. For example, the expandable section 204 can comprise convoluted folds of the wall of the tubing, such that when the tubing 202 is pressurized from P1 to P2 the expandable section 204 increases in length from L1 to L2. In one variation, the non-expandable section 206 of the tubing 202 is affixed within the lumen 178 in the first material 184 such that elongation of the expandable section 204 causes outward movement of the tip.

The invention claimed is:

1. An expandable tubing comprising:
   an outer tube body comprising a lumen; and
   a spring material within the outer tube body,
   where the spring material extends helically around the lumen at least one full turn in a continuous undulating manner within the outer tube body, and
   where an entire turn of the at least one full turn of the spring material is expandable and contractible.

2. The expandable tubing of claim 1, where the spring material is configured to assist the outer tube body in expanding when a device is passed through the lumen of the outer tube body, and
   where the spring material is expandable and contractible such that expansion of the spring material expands a diameter of the outer tube body.

3. The expandable tubing of claim 1, where the outer tube body is expandable by advancing a device into the lumen, and where the outer tube body is contractible by withdrawing the device from the lumen.

4. The expandable tubing of claim 1, where the outer tube body has a natural state and an expanded state,
   where when the outer tube body is in the natural state, the spring material is biased to expand a diameter of the outer tube body,
   where when the outer tube body is in the expanded state, the outer tube body is biased to contract the diameter of the outer tube body,
   where the outer tube body is expandable from the natural state to the expanded state by advancing a device in the lumen,
   where the outer tube body is contractible from the expanded state to the natural state by withdrawing the device from the lumen,
   where the spring material has a first shape when the outer tube body is in the natural state, and
   where the spring material has a second shape different than the first shape when the outer tube body is in the expanded state.

5. The expandable tubing of claim 1, where the spring material is configured to reduce a force required to expand a diameter of the outer tube body via a device by naturally reverting to a more expanded configuration as the device is advanced in the lumen.

6. The expandable tubing of claim 1, where the outer tube body has a natural state and an expanded state,
   where the outer tube body is expandable from the natural state to the expanded state due to a device in the lumen such that when the device is advanced in the lumen the spring material is configured to reduce a force required to expand a diameter of the outer tube body via the device by naturally reverting to a more expanded configuration as the device is advanced in the lumen, and
   where the outer tube body is contractible from the expanded state to the natural state due to the device in the lumen such that when the device is retracted from the lumen the outer tube body is configured to contract the diameter of the outer tube body.

7. The expandable tubing of claim 1, where the outer tube body has a natural state and an expanded state,
   where when the outer tube body is in the natural state, the spring material is biased to expand a diameter of the outer tube body,
   where when the outer tube body is in the expanded state, the outer tube body is biased to contract the diameter of the outer tube body,
   where the outer tube body is expandable from the natural state to the expanded state due to a device in the lumen such that when the device is advanced in the lumen the spring material is configured to reduce a force required to expand the diameter of the outer tube body via the device by naturally reverting to a more expanded configuration as the device is advanced in the lumen,
   where the outer tube body is contractible from the expanded state to the natural state due to the device in the lumen such that when the device is retracted from the lumen the outer tube body is configured to contract the diameter of the outer tube body,
   where the spring material has a first shape when the outer tube body is in the natural state, and
   where the spring material has a second shape different than the first shape when the outer tube body is in the expanded state.

8. The expandable tubing of claim 7, further comprising a coil or a braid in the outer tube body.

9. The expandable tubing of claim 1, where the continuous undulating manner comprises a zig-zag manner.

10. The expandable tubing of claim 1, where the spring material comprises a zig-zag wire.

11. The expandable tubing of claim 1, where the spring material comprises peaks and valleys, and where adjacent peaks are in adjacent valleys.

12. The expandable tubing of claim 1, where the spring material has a zig-zag pattern comprising peaks and valleys, and where adjacent peaks are separated from adjacent valleys by a gap.

13. The expandable tubing of claim 1, further comprising a coil or a braid in the outer tube body.

14. The expandable tubing of claim 1, where adjacent turns of the spring material are separated by a gap, and where the gap is less than a peak-to-peak amplitude of the continuous undulating manner in a turn of the spring material.

15. The expandable tubing of claim 1, where the continuous undulating manner of the spring material comprises peaks and valleys, where the peaks of adjacent turns of the spring material are separated by a gap, and where the gap is less than a peak-to-peak amplitude of two adjacent peaks in a single turn of the spring material.

16. The expandable tubing of claim 1, where the spring material extends helically around the lumen at least a first full turn and a second full turn in the continuous undulating manner within the outer tube body, where the continuous undulating manner of the spring material comprises peaks and valleys, and where a gap between the first full turn and the second full turn is less than a peak-to-peak amplitude between a first peak of the first full turn and a second peak of the first full turn.

17. The expandable tubing of claim 1, where the spring material extends helically around the lumen multiple turns in the continuous undulating manner within the outer tube body, where the continuous undulating manner of the spring material comprises peaks and valleys, and where peaks of adjacent turns are aligned with each other longitudinally along a length of the outer tube.

18. The expandable tubing of claim 1, further comprising a material that extends helically around the lumen, where the material is on a radial inside of the spring material or on a radial outside of the spring material.

19. An expandable tubing comprising:
an outer tube body comprising a lumen;
a coil or a braid in the outer tube body; and
a spring material wound in an undulating manner within the outer tube body,
where the spring material extends around the lumen,
where the outer tube body is expandable via the spring material,
where the spring material is contractible via the outer tube body, and
where the coil or the braid extends around the lumen on a radial inside or on a radial outside of the spring material.

20. The expandable tubing of claim 19, where the coil or the braid extends helically around the lumen on the radial inside or on the radial outside of the spring material.

21. The expandable tubing of claim 19, where the spring material comprises a zig-zag wire.

22. An expandable tubing comprising:
an outer tube body comprising a lumen; and
a spring material within the outer tube body,
where the spring material extends around the lumen,
where the spring material is expandable and contractible,
where the spring material extends helically around the lumen a first full turn and a second full turn in a continuous undulating manner within the outer tube body, where the first full turn is adjacent the second full turn, where the continuous undulating manner of the spring material comprises peaks and valleys, and where a peak of the first full turn is in a valley of the second full turn.

23. The expandable tubing of claim 22, where the spring material comprises a zig-zag wire.

* * * * *